(12) United States Patent
Nishijima et al.

(10) Patent No.: US 11,874,409 B2
(45) Date of Patent: Jan. 16, 2024

(54) CORRECTION X-RAY DETECTOR, X-RAY CT APPARATUS, AND DETECTOR ELEMENT DETERMINING METHOD

(71) Applicant: CANON MEDICAL SYSTEMS CORPORATION, Otawara (JP)

(72) Inventors: Akira Nishijima, Nasushiobara (JP); Koichi Miyama, Otawara (JP); Yasuo Saito, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 44 days.

(21) Appl. No.: 17/304,951

(22) Filed: Jun. 29, 2021

(65) Prior Publication Data

US 2022/0003881 A1 Jan. 6, 2022

(30) Foreign Application Priority Data

Jul. 6, 2020 (JP) .................................. 2020-116571
May 28, 2021 (JP) .................................. 2021-089839

(51) Int. Cl.
| | | |
|---|---|---|
| G01T 1/164 | (2006.01) | |
| G21K 1/02 | (2006.01) | |
| A61B 6/03 | (2006.01) | |

(52) U.S. Cl.
CPC .............. *G01T 1/1648* (2013.01); *A61B 6/03* (2013.01); *G21K 1/02* (2013.01)

(58) Field of Classification Search
CPC ....... G01T 1/1648; G01T 1/2985; A61B 6/03; A61B 6/032; A61B 6/06; A61B 6/4233; A61B 6/58; G21K 1/02
See application file for complete search history.

(56) References Cited

U.S. PATENT DOCUMENTS

| | | | |
|---|---|---|---|
| 10,310,098 B1* | 6/2019 | Qiang | ..................... G01T 1/202 |
| 2005/0259784 A1* | 11/2005 | Wu | .......................... A61B 6/585 |
| | | | 378/19 |
| 2011/0075909 A1* | 3/2011 | Kanagawa | ............. A61B 6/586 |
| | | | 378/4 |
| 2012/0177174 A1* | 7/2012 | Ikhlef | ..................... A61B 6/585 |
| | | | 378/207 |
| 2013/0168750 A1 | 7/2013 | Ikhlef et al. | |
| 2013/0168796 A1 | 7/2013 | Ikhlef et al. | |
| 2017/0020475 A1* | 1/2017 | Spahn | .................. A61B 6/5258 |

FOREIGN PATENT DOCUMENTS

| | | | |
|---|---|---|---|
| JP | 2013-140962 A | | 7/2013 |
| JP | 2013-140975 A | | 7/2013 |
| JP | 2019-113392 A | | 7/2019 |
| JP | 2020179039 A | * | 11/2020 ............... A61B 6/03 |

* cited by examiner

*Primary Examiner* — David P Porta
*Assistant Examiner* — Gisselle M Gutierrez
(74) *Attorney, Agent, or Firm* — Oblon, McClelland, Maier & Neustadt, L.L.P.

(57) ABSTRACT

A correction X-ray detector according to an embodiment includes a plurality of detector elements configured to detect an X-ray, and processing circuitry. The processing circuitry is configured to acquire a plurality of output values respectively corresponding to the plurality of the plurality of detector elements. The processing circuitry is further configured to determine the detector elements to be used in generating correction data based on the plurality of output values.

16 Claims, 10 Drawing Sheets

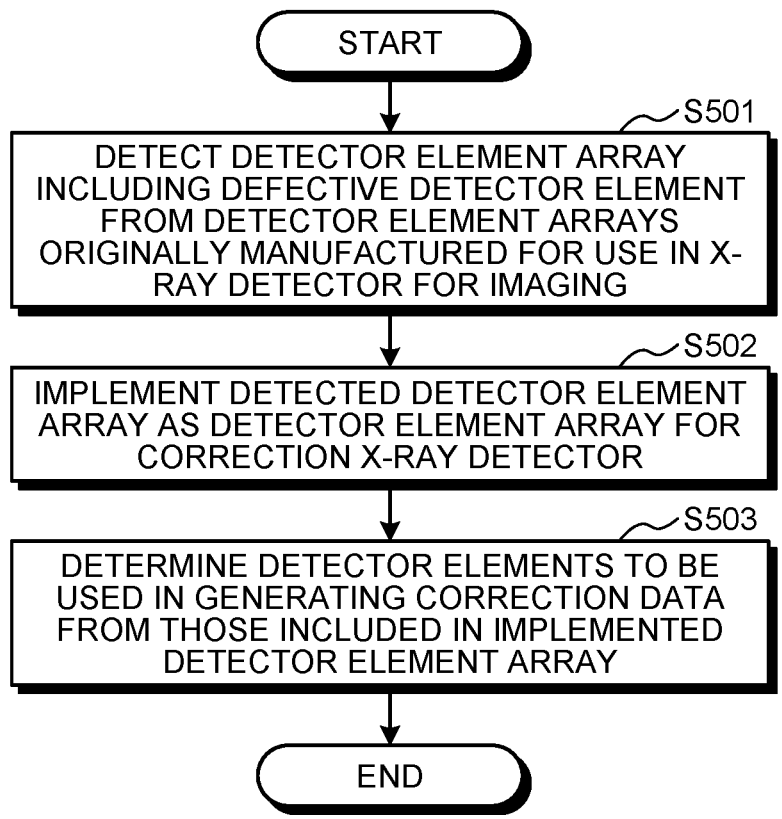

CORRECTION X-RAY DETECTOR, X-RAY CT APPARATUS, AND DETECTOR ELEMENT DETERMINING METHOD

CROSS-REFERENCE TO RELATED APPLICATIONS

This application is based upon and claims the benefit of priority from Japanese Patent Application No. 2020-116571, filed on Jul. 6, 2020 and Japanese Patent Application No. 2021-089839, filed on May 28, 2021; the entire contents of which are incorporated herein by reference.

FIELD

Embodiments described herein relate generally to a correction X-ray detector, an X-ray CT apparatus, and a detector element determining method.

BACKGROUND

Recently having come to be known is a technology making use of, in an X-ray computed tomography (CT) apparatus, a correction X-ray detector for correcting variations in the X-rays emitted from the X-ray tube, in addition to an X-ray detector for imaging. Generally speaking, although the number of such correction X-ray detectors required in an X-ray CT apparatus is one, because the correction X-ray detectors require dedicated designing, costs and development hours have been an issue that needs to be addressed.

BRIEF DESCRIPTION OF THE DRAWINGS

FIG. 12 is a flowchart illustrating a detector element determining method according to a fifth embodiment.

DETAILED DESCRIPTION

Figure 1:
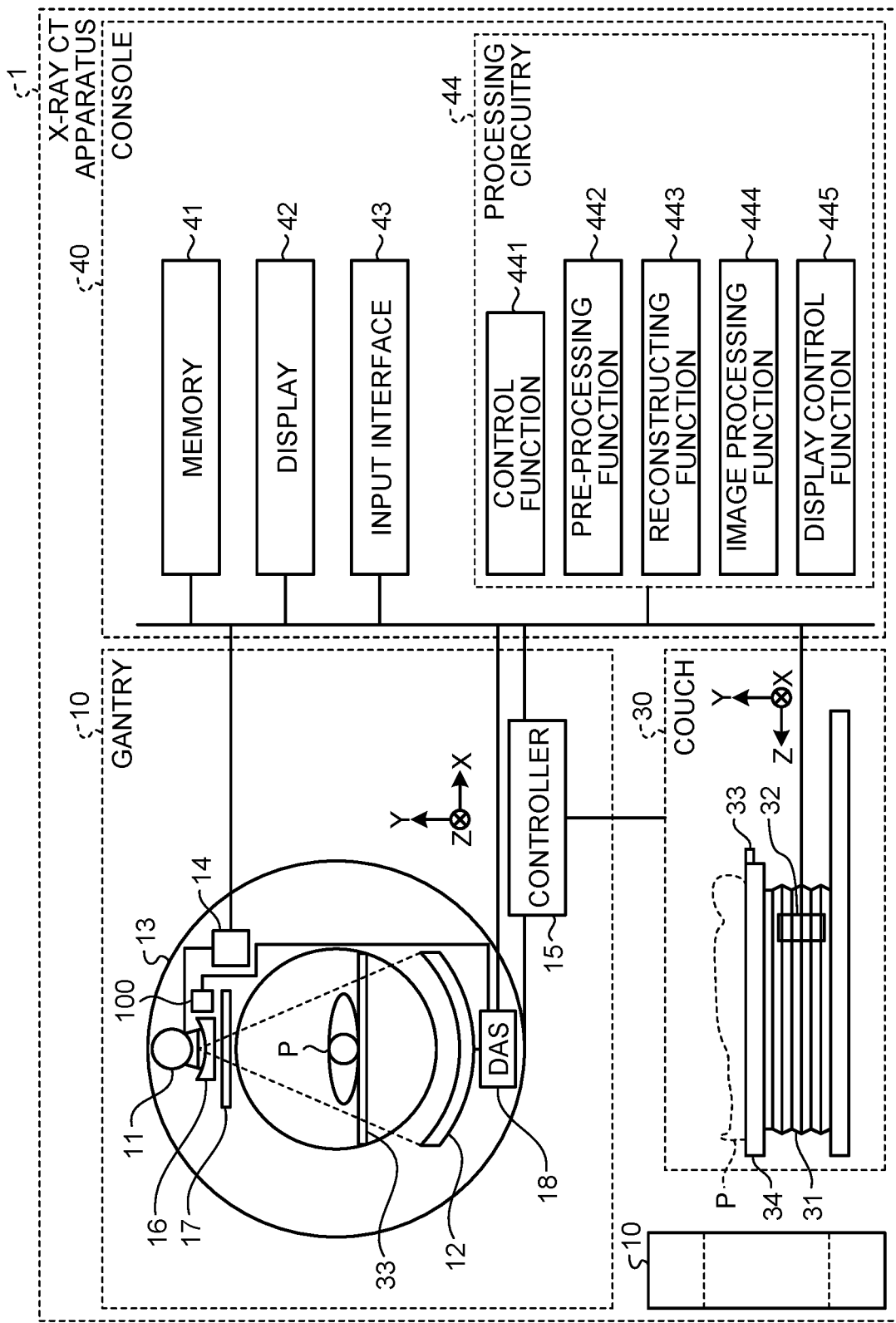
FIG. 1 is a schematic illustrating an exemplary configuration of an X-ray CT apparatus according to a first embodiment.

A correction X-ray detector according to an embodiment includes a plurality of detector elements configured to detect an X-ray, and processing circuitry. The processing circuitry is configured to acquire a plurality of output values respectively corresponding to the plurality of the plurality of detector elements. The processing circuitry is further configured to determine the detector elements to be used in generating correction data based on the plurality of output values.

A correction X-ray detector, an X-ray CT apparatus, and a detector element determining method according to some embodiments to be disclosed herein will now be explained with reference to some drawings. The configurations illustrated in each of the drawings are merely schematic representations, and the sizes of the elements or the ratios between the sizes of the elements illustrated in the drawings may be different from those of the actual elements. Furthermore, the sizes of the same elements or the ratios between the sizes of the same elements are sometimes represented differently among some of the drawings.

First Embodiment

FIG. 1 is a schematic illustrating an exemplary configuration of an X-ray CT apparatus according to a first embodiment.

For example, as illustrated in FIG. 1, this X-ray CT apparatus 1 according to the embodiment includes a gantry 10, a couch 30, and a console 40.

In this embodiment, the rotational axis of an un-tilted rotating frame 13 or the longitudinal direction of a couchtop 33 of the couch 30 is defined as a Z axis direction. The axis direction that perpendicularly intersects with the Z axis direction and that is horizontal to the floor surface is defined as an X axis direction. The axis direction that perpendicularly intersects with the Z axis direction and that is also perpendicular to the floor surface is defined as a Y axis direction.

The gantry 10 is a device that emits X-rays toward a subject P such as a patient, that detects the X-rays passed through the subject P, and that makes outputs to the console 40. Specifically, the gantry 10 includes an X-ray tube 11, an X-ray detector 12, the rotating frame 13, an X-ray high voltage device 14, a controller 15, a wedge 16, an X-ray aperture 17, and a data acquisition system (DAS) 18. In FIG. 1, although the gantry 10 viewed in X axis direction and the gantry 10 viewed in the Z axis direction are both illustrated for the convenience of explanations, the X-ray CT apparatus 1 has only one gantry 10.

The X-ray tube 11 is a vacuum tube having a cathode (filament) that generates thermal electrons, and an anode (target) with which the thermal electrons collide and that generates X-rays thereby. Specifically, the X-ray tube 11 generates X-rays by receiving an application of a high voltage from the X-ray high voltage device 14 and causing the cathode to emit thermal electrons toward the anode. For example, the X-ray tube 11 is a rotating-anode type X-ray tube that generates X-rays by emitting thermal electrons toward a rotating anode.

The X-ray detector 12 includes a plurality of detector elements configured to detect the X-rays to be emitted from the X-ray tube 11 and passed through the subject P, and outputs an electric signal corresponding to the dose of X-rays detected by each of the detector elements to the DAS 18. Specifically, the X-ray detector 12 has a structure that includes a plurality of rows of the detector elements, the rows being an arrangement of the detector elements in a channel direction extending along the circumferential direction of an arc about the focal point of the X-ray tube 11, and in which the rows of the detector elements are arranged along a slice direction (also referred to as a row direction).

For example, the X-ray detector 12 is an indirect conversion detector that includes a collimator, a scintillator array, and a detector element array. The collimator is disposed on a surface of the scintillator array, on the incoming side of the X-rays, and is provided with an X-ray shield that absorbs the scattered X-rays. The collimator is a one-dimensional or a two-dimensional collimator, for example. The collimator is also referred to as a grid. The scintillator array is disposed on a surface of the detector element array, on the incoming side of the X-rays, and includes a plurality of scintillators. Each of the scintillators has a scintillator crystal that emits light having the quantity of photons corresponding to the dose of X-rays becoming incident thereon. The detector element array has a plurality of detector elements, and each of the detector elements converts the quantity of light output from the scintillator into an electric signal in accordance with the quantity of light. For example, the detector element array is configured as a plurality of sub-arrays that are arranged side by side in the channel direction and the slice direction. Each of the sub-arrays includes a plurality of detector elements arranged one dimensionally (n rows×one column) or two dimensionally (n rows×m columns) on the same plane. An example of such a detector element is a light receiving element such as a photodiode (PD) or a photomultiplier tube (PMT).

The rotating frame 13 is an annular frame by which the X-ray tube 11 and the X-ray detector 12 are rotated about a rotational axis (Z axis). Specifically, the rotating frame 13 is rotatably supported by a fixed frame (not illustrated) about a rotational axis, with the X-ray tube 11 and the X-ray detector 12 supported thereby in a manner facing each other. The rotating frame 13 is then rotated about the rotational axis under the control of the controller 15, thereby causing the X-ray tube 11 and the X-ray detector 12 to be rotated about the rotational axis. In addition to the X-ray tube 11 and the X-ray detector 12, the rotating frame 13 also includes and supports the X-ray high voltage device 14 and the DAS 18.

The X-ray high voltage device 14 includes a high voltage generator device that has a function for generating a high voltage to be applied to the X-ray tube 11, and an X-ray controller that controls the output voltage based on the X-rays to be output from the X-ray tube 11. The high voltage generator device has electric circuits such as a transformer and a rectifier, and may be a transformer-type high voltage generator or an inverter-type high voltage generator. The X-ray high voltage device 14 may be provided on the rotating frame 13, or may be provided on the fixed frame (not illustrated) rotatably supporting the rotating frame 13, in the gantry 10.

The wedge 16 is a filter for adjusting the dose of X-rays emitted from the X-ray tube 11. Specifically, the wedge 16 is a filter that passes and attenuates the X-rays emitted toward the subject P from the X-ray tube 11 so that the X-rays output from the X-ray tube 11 has a predetermined distribution. For example, the wedge 16 is a filter made of aluminum processed to have a given target angle and a given thickness. The wedge 16 is also referred to as a wedge filter or a bow-tie filter.

The X-ray aperture 17 is a lead plate for adjusting the range to be irradiated with the X-rays having passed through the wedge 16, and has a slit formed by a combination of a plurality of lead plates, for example.

The DAS 18 is processing circuitry that generates detection data based on the electric signals output from the detector elements of the X-ray detector 12. Specifically, the DAS 18 generates the detection data by amplifying the electric signals output from the detector elements of the X-ray detector 12, and converting the amplified electric signals from the analogue signals into digital signals. The detection data generated by the DAS 18 is then transmitted by a transmitter that has a light-emitting diode (LED) and is provided to the rotating frame 13, to a receiver having a photodiode and provided to a non-rotating portion of the gantry 10 (e.g., the support frame), via an optical communication, and is then transferred to the console 40. The method for transmitting the detection data from the rotating frame 13 to the non-rotating portion of the gantry 10 is not limited to the optical communication, but any other method may be used, as long as the data can be transferred contactlessly.

The controller 15 includes a driving mechanism such as a motor and an actuator, and processing circuitry that controls the driving mechanism. The controller 15 has a function for controlling operations of the gantry 10 and the couch 30 by receiving input signals from the console 40 or an input interface 43, which will be described later, mounted on the gantry 10. By receiving input signals, the controller 15 control to rotate the rotating frame 13, control to tilt the gantry 10, and control to cause the couch 30 and the couchtop 33 to operate, for example. The control for tilting the gantry 10 is implemented by causing the controller 15 to rotate the rotating frame 13 about an axis that is in parallel with the X axis direction, based on inclination angle (tilt angle) information input from the input interface 43 that is mounted on the gantry 10. The controller 15 may be provided either to the gantry 10 or the console 40.

The couch 30 is a device where the subject P to be scanned is laid and that moves the subject P, and includes a base 31, a couch driving device 32, a couchtop 33, and a support frame 34. The base 31 is a housing that supports the support frame 34 movably in the vertical directions. The couch driving device 32 is a motor or an actuator for moving the couchtop 33 where the subject P is laid, in the long axis directions of the couchtop 33. The couchtop 33 provided on the top surface of the support frame 34 is a plate on which the subject P is laid. The couch driving device 32 may also be configured to move the support frame 34, in addition to the couchtop 33, in the long axis directions of the couchtop 33.

The console 40 is a device that receives operations for the X-ray CT apparatus 1 from an operator, and reconstructs CT image data using detection data collected by the gantry 10. The console 40 includes a memory 41, a display 42, the input interface 43, and processing circuitry 44. Explained herein is an example in which the console 40 and the gantry 10 are separate units, but the console 40 or some of the elements of the console 40 may be included in the gantry 10.

The memory 41 is implemented as a random access memory (RAM), a semiconductor memory device such as a flash memory, a hard disk, or an optical disk, for example. The memory 41 stores therein projection data and CT image data, for example.

The display 42 displays various types of information. For example, the display 42 outputs medical images (CT images) generated by the processing circuitry 44, graphical user interfaces (GUIs) for receiving various operations from the operator, and the like. The display 42 is a liquid-crystal display or a cathode ray tube (CRT) display, for example. The display 42 may be provided to the gantry 10, for example. The display 42 may also be a desktop display, or may be provided as a tablet terminal capable of wirelessly communicating with the main unit of the console 40, for example.

The input interface 43 receives various input operations from the operator, converts the received input operations into electric signals, and outputs the electric signals to the processing circuitry 44. The input interface 43 receives, for example, a collecting condition for collecting the projection data, a reconstructing condition for reconstructing the CT image data, or an image processing condition for generating a post-processed image from the CT image, from the operator. The input interface 43 is implemented as, for example, a mouse, a keyboard, a trackball, a switch, a button, a joystick, a touch pad on which an input operation is made by touching the operation surface, a touch screen in which a display screen and a touch pad are integrated, a contactless input circuit using an optical sensor, and an audio input circuit. The input interface 43 may also be provided to the gantry 10, for example. The input interface 43 may also be provided as a tablet terminal capable of wirelessly communicating with the main unit of the console 40, for example. Furthermore, the input interface 43 is not limited to any interface provided with physical operation components such as a mouse or a keyboard. For example, another example of the input interface 43 includes an input interface that receives an electric signal corresponding to an input operation made via an external input device provided separately from the console 40, and outputs the signal to the processing circuitry 44.

The processing circuitry 44 controls the operations of the entire X-ray CT apparatus 1. The processing circuitry 44 includes a control function 441, a pre-processing function 442, a reconstructing function 443, an image processing function 444, and a display control function 445.

The control function 441 controls each of the units included in the X-ray CT apparatus 1, based on an input operation received from the operator via the input interface 43. The control function 441 controls, for example, a CT scan by controlling the X-ray high voltage device 14, the controller 15, and the DAS 18. The control function 441 also controls generating and displaying CT image data by controlling the pre-processing function 442, the reconstructing function 443, the image processing function 444, and the display control function 445.

The pre-processing function 442 generates projection data resultant of applying pre-processing, such as logarithmic transformation, offset correction, channel sensitivity correction, and beam hardening correction, to the detection data output from the DAS 18. The data before the pre-processing (detection data) and the data after the pre-processing are sometimes collectively referred to as projection data.

The reconstructing function 443 generates CT image data (reconstruction image data) by performing a reconstruction using filtered back projection, iterative reconstruction, or the like, of the projection data generated by the pre-processing function 442.

The image processing function 444 converts the CT image data generated by the reconstructing function 443 into slice image data representing a slice, or image data rendered from some viewpoint direction, for example. Specifically, by performing known three-dimensional image processing to the CT image data based on an input operation received from the operator via the input interface 43, the image processing function 444 converts the image data into tomographic slice image data representing a slice, or image data rendered from some viewpoint direction. Examples of the three-dimensional image processing include volume rendering, surface rendering, image value projection, multi-planar reconstruction (MPR), and curved MPR (CPR). The three-dimensional image processing may also be directly performed by the reconstructing function 443.

The display control function 445 causes the display 42 to display images based on various types of image data generated by the reconstructing function 443 and the image processing function 444. For example, the display control function 445 causes the display 42 to display a CT image based on the CT image data, a slice image based on the slice image data representing a slice, a rendering image from a viewpoint direction based on the image data rendered from the viewpoint direction. The display control function 445 also causes the display 42 to a display image for presenting an operation screen, for example.

The processing circuitry 44 is implemented by a processor, for example. With such an implementation, each of the processing functions included in the processing circuitry 44 is stored in the memory 41 as a computer-executable program. The processing circuitry 44 implements the processing function corresponding to each of the computer programs by reading the computer program from the memory 41 and executing the computer program. In other words, the processing circuitry 44 having read the computer programs comes to have the processing functions illustrated inside the processing circuitry 44 in FIG. 1.

The overall configuration of the X-ray CT apparatus 1 according to the embodiment has been explained above. Given such a configuration, the X-ray CT apparatus 1 according to the embodiment also includes a correction X-ray detector 100 for correcting the X-rays to be emitted from the X-ray tube 11, in addition to the X-ray detector 12 used for imaging.

The correction X-ray detector 100 detects the X-rays emitted from the X-ray tube 11, and generates correction data for correcting the X-ray variations.

However, generally speaking, although the number of such correction X-ray detectors required in an X-ray CT apparatus is one, because such a detector requires dedicated designing, costs and development hours have been an issue that needs to be addressed.

To address this issue, the X-ray CT apparatus 1 according to the embodiment is configured to reduce the implementation cost of the correction X-ray detector 100.

Specifically, the correction X-ray detector 100 includes a plurality of detector elements configured to detect X-rays, an acquiring unit configured to acquire a plurality of output values that correspond to the respective detector elements, and a determining unit configured to determine the detector elements to be used in generating the correction data based on the output values.

With such a configuration, when the detector elements include some defective detector element, the detector elements other than the defective detector element can be used to generate the correction data. In this manner, it becomes possible to use the detector elements originally manufactured for the use in the X-ray detector 12 used for imaging but rendered not usable because a defective detector element is included, as those for the correction X-ray detector 100. Hence, the correction X-ray detector 100 can be manufactured at a lower cost. Therefore, according to the embodiment, it is possible to reduce the implementation cost of the correction X-ray detector 100.

The correction X-ray detector 100 and the X-ray CT apparatus 1 according to the embodiment will now be explained in detail. In this embodiment, an example in which the correction X-ray detector 100 has one channel will be explained.

Figure 2:
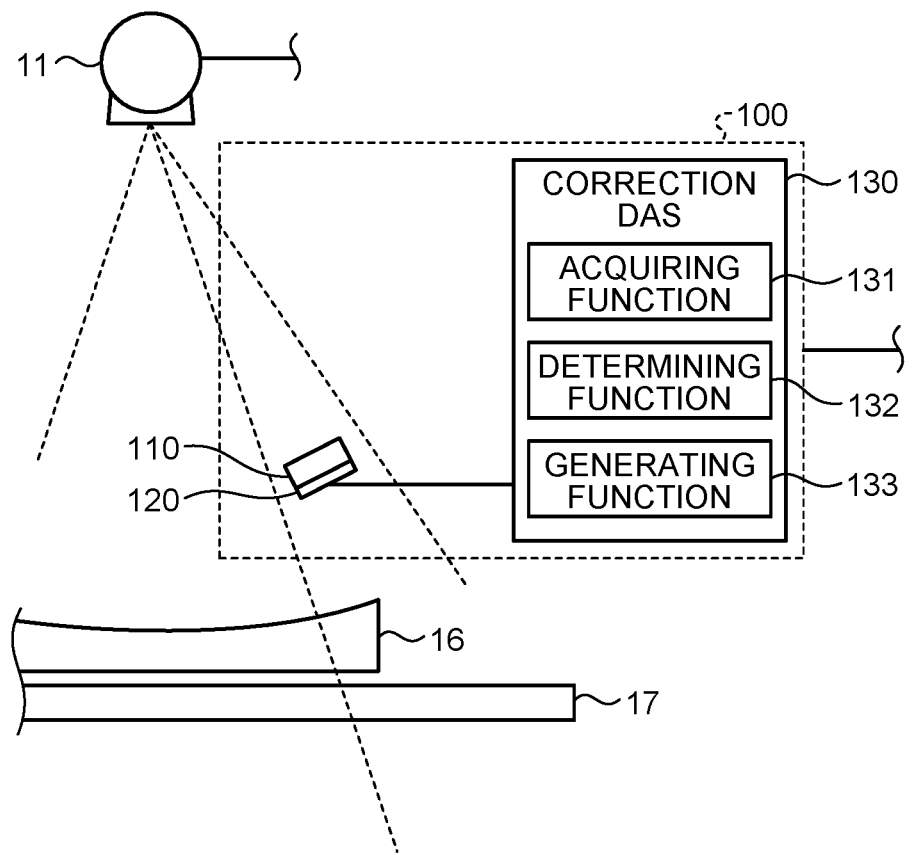
FIG. 2 is a schematic illustrating an exemplary configuration of a correction X-ray detector according to the first embodiment.

FIG. 2 is a schematic illustrating an exemplary configuration of the correction X-ray detector 100 according to the first embodiment.

For example, as illustrated in FIG. 2, the correction X-ray detector 100 is provided as a unit separate from the X-ray detector 12 used for imaging, and is fixed to the rotating frame 13 included in the gantry 10, with a support member (not illustrated) such as a rigid frame. At this time, the correction X-ray detector 100 is provided so as not to enter the imaging range of the X-ray detector 12, between the X-ray tube 11 and the wedge 16. With this configuration, the X-rays being incident on the correction X-ray detector 100 do not experience the changes introduced by the wedge 16 or the X-ray aperture 17. It is also possible for the correction X-ray detector 100 to be integrated with the wedge 16 or the X-ray aperture 17.

The correction X-ray detector 100 then detects the X-rays emitted from the X-ray tube 11, and generates correction data for correcting the X-ray variations. The correction data generated by the correction X-ray detector 100 is then transferred to the console 40 via the DAS 18, and is used in correcting the variations in the dose of the X-rays to be emitted from the X-ray tube 11.

Specifically, the correction X-ray detector 100 includes a scintillator array 110, a detector element array 120, and a correction DAS 130.

Figure 3:
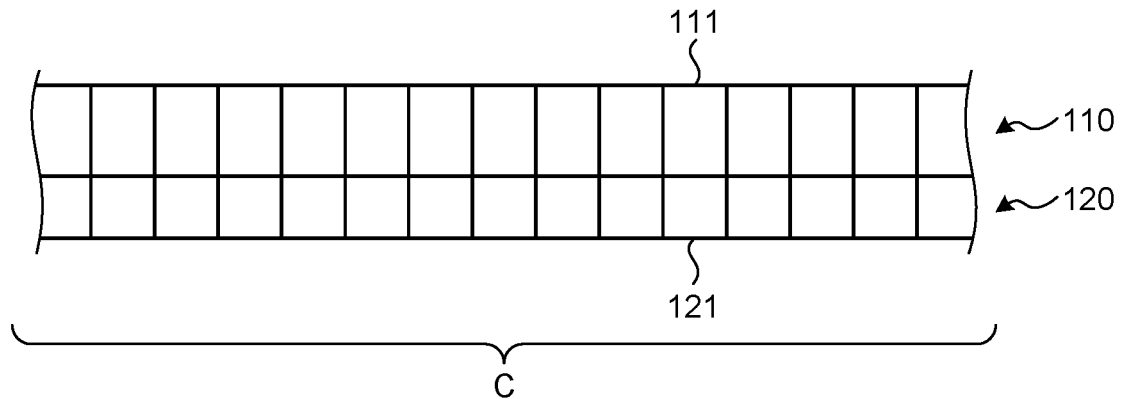
FIG. 3 is a schematic illustrating one example of a scintillator array and a detector element array included in the correction X-ray detector according to the first embodiment.

FIG. 3 is a schematic illustrating one example of the scintillator array 110 and the detector element array 120 included in the correction X-ray detector 100 according to the first embodiment.

For example, as illustrated in FIG. 3, the scintillator array 110 is disposed on a surface of the detector element array 120 on the incoming side of the X-rays, and includes a plurality of scintillators 111. Each of the scintillators 111 has a scintillator crystal that emits light having a photon quantity corresponding to the dose of the X-rays incident thereon.

The detector element array 120 has a plurality of detector elements 121, and each of the detector elements 121 converts the quantity of light emitted from the scintillator 111 into an electric signal in accordance with the quantity of light. For example, the detector element array 120 includes a plurality of detector elements that are arranged one dimensionally (n rows×one column) or two-dimensionally (n rows×m column) on the same plane. An example of such a detector element is a light receiving element such as a PD or a PMT.

The detector elements 121 included in the detector element array 120 are those originally manufactured for the use in the X-ray detector 12 for imaging, for example. For example, sub-arrays of detector elements that are manufactured for the X-ray detector 12 for imaging are used in the detector element array 120.

In this embodiment, a channel C is assigned to at least one part of the detector elements 121 included in the detector element array 120. For example, the channel C is assigned to the entire detector elements 121 included in the detector element array 120.

In the example illustrated in FIG. 3, the number of scintillators 111 included in the scintillator array 110 is equal to the number of the detector elements 121 included in the detector element array 120, but the number of the scintillators 111 may be different from, or the same as that of the detector elements 121. For example, the scintillator array 110 may be configured in such a manner that each of the scintillators 111 is disposed on top of corresponding one of the detector elements 121, or for each of the scintillators 111 to be disposed on top of a plurality of the detector elements 121. Furthermore, for example, the scintillator array 110 may cover the entire detector elements 121 or only the detector elements 121 assigned to the channel C, among those included in the detector element array 120.

Referring back to FIG. 2, the correction DAS 130 is processing circuitry that generates the correction data based on the electric signals output from the detector elements 121 in the detector element array 120. Specifically, the correction DAS 130 generates the correction data by amplifying the electric signals output from the detector elements 121 included in the detector element array 120, and converting the amplified electric signals from the analogue signals into digital signals.

Specifically, the correction DAS 130 includes an acquiring function 131, a determining function 132, and a generating function 133. The acquiring function 131 is one example of the acquiring unit. The determining function 132 is one example of the determining unit. The generating function 133 is one example of the generating unit.

The acquiring function 131 acquires a plurality of output values that correspond to the respective detector elements 121 included in the detector element array 120.

Specifically, the acquiring function 131 acquires the output values of the electric signals output from the respective detector elements 121 included in the detector element array 120, the electric signals being output when the scintillator array 110 in the correction X-ray detector 100 is irradiated with the X-rays of the X-ray tube 11.

The determining function 132 determines the detector elements to be used in generating the correction data based on the output values acquired by the acquiring function 131.

Specifically, the determining function 132 performs thresholding to the output values acquired by the acquiring function 131, and determines the detector elements to be used in generating the correction data based on the result of the thresholding.

At this time, the determining function 132 determines the detector elements 121 to be used in generating the correction data, from those to which the channel is assigned.

Figure 4:
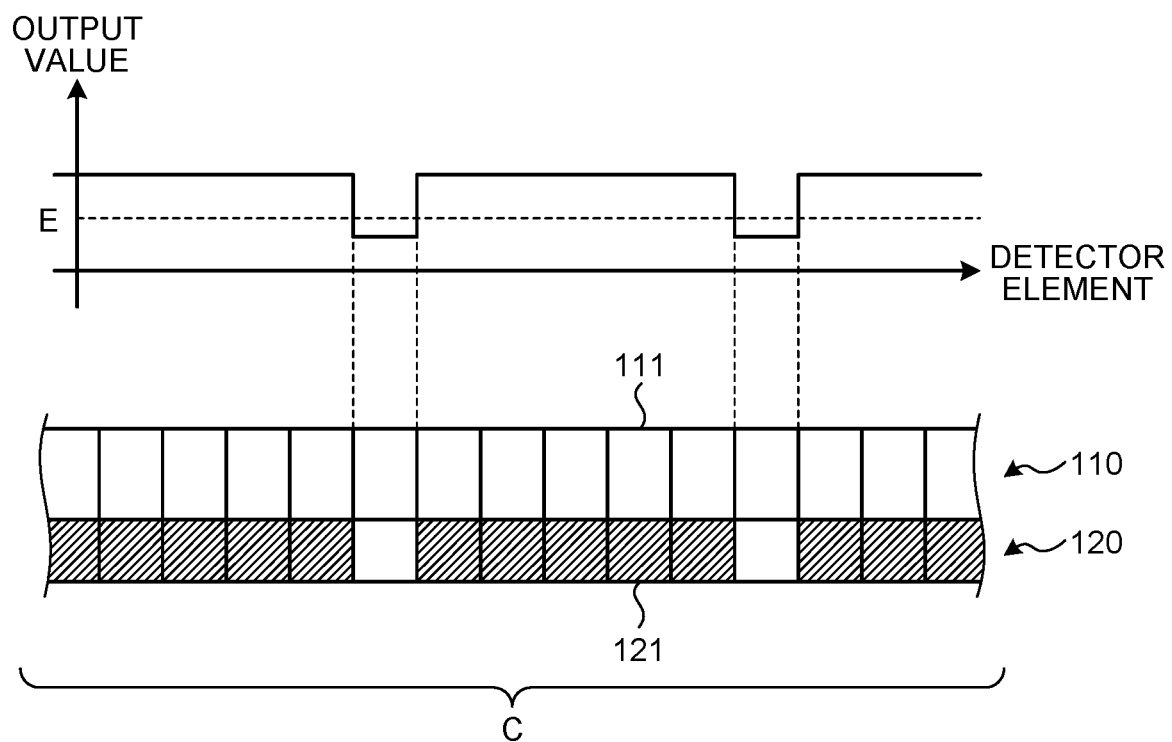
FIG. 4 is a schematic illustrating one example of how detector elements are determined by a determining function according to the first embodiment.

FIG. 4 is a schematic illustrating one example of how detector elements are determined by the determining function 132 according to the first embodiment.

For example, as illustrated in FIG. 4, the determining function 132 detects the detector element 121 the output value of which is smaller than an expected value E, among the detector elements 121 assigned to the channel C. The determining function 132 determines the detector elements 121 other than the detected detector element 121 as the detector elements to be used in generating the correction data. In the example illustrated in FIG. 4, the detector elements 121 determined as the detector elements to be used in generating the correction data are hatched with diagonals.

The expected value E herein is a threshold for distinguishing whether a detector element 121 is sufficiently capable of detecting the X-rays. The expected value E is set in advance, for example, based on an actual measurement or a standard value, during the installation of the correction X-ray detector 100 in an installation site such as a hospital.

With this configuration, when the detector element array 120 includes some defective detector element 121 that outputs an output value smaller than the expected value E, the detector elements 121 is excluded from the detector elements that are used in generating the correction data. As a result, when the detector elements 121 include some defective detector element, correction data can be generated using the detector elements 121 other than the defective detector elements 121.

Referring back to FIG. 2, the generating function 133 generates the correction data based on the detector elements determined by the determining function 132.

Specifically, the generating function 133 generates the correction data using the sum of the output values from the detector elements having been determined by the determining function 132. Alternatively, the generating function 133 may also generate the correction data using the average or the maximum value of the output values from the detector elements, for example.

The correction data thus generated by the generating function 133 is transferred to the console 40 via the DAS 18, and is stored in the memory 41. The correction data stored in the memory 41 is then read by the processing circuitry 44, and used in correcting the variations in the dose of the X-rays to be emitted from the X-ray tube 11.

The correction DAS 130 is implemented by a processor, for example. With such an implementation, each of the processing functions included in the correction DAS 130 is stored in a memory (not illustrated) as a computer-executable program. The correction DAS 130 then implements the processing function corresponding to the respective computer programs by reading the computer programs from the memory, and executing the computer programs. In other words, the correction DAS 130 having read the computer programs comes to have the processing functions illustrated inside of the correction DAS 130 in FIG. 2.

Figure 5:
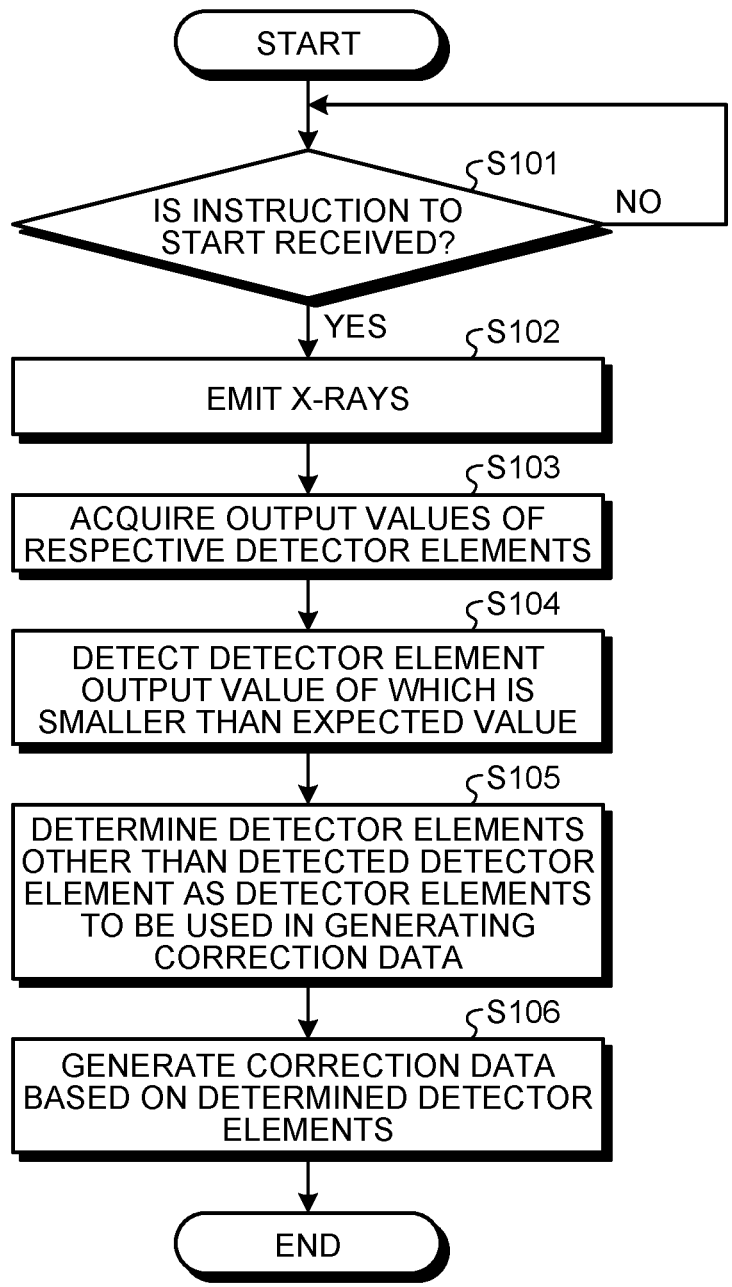
FIG. 5 is a flowchart illustrating the sequence of a process performed by the X-ray CT apparatus according to the first embodiment.

FIG. 5 is a flowchart illustrating the sequence of a process performed by the X-ray CT apparatus 1 according to the first embodiment.

The process explained below is performed during the installation of the X-ray CT apparatus 1 in an installation site such as a hospital, or during an adjustment of the X-ray CT apparatus 1, for example.

For example, as illustrated in FIG. 5, to begin with, when an instruction to start is received from an operator via the input interface 43 (Yes at Step S101), the processing circuitry 44 causes the X-ray tube 11 to emit the X-rays toward the scintillator array 110 in the correction X-ray detector 200, by controlling the X-ray high voltage device 14 (Step S102). This step is a step corresponding to the control function 441. At this step, for example, the control function 441 is implemented by causing the processing circuitry 44 to read the computer program corresponding to the control function 441 from the memory 41, and executing the computer program.

The correction DAS 130 then acquires the output values that correspond to the respective detector elements 121 included in the detector element array 120 (Step S103). This step is a step corresponding to the acquiring function 131. At this step, the acquiring function 131 is implemented by causing the correction DAS 130 to read the computer program corresponding to the acquiring function 131 from the memory, and executing the computer program, for example.

The correction DAS 130 then detects the detector element 121 the output value of which is smaller than the expected value, from those to which the channel is assigned, based on the acquired output values (Step S104). The correction DAS 130 then determines the detector elements 121 other than the detected detector element 121 as the detector elements to be used in generating the correction data (Step S105). These steps are steps corresponding to the determining function 132. At these steps, the determining function 132 is implemented by causing the correction DAS 130 to read the computer program corresponding to the determining function 132 from the memory, and executing the computer program, for example.

The correction DAS 130 then generates the correction data based on the determined detector elements (Step S106). This step is a step corresponding to the generating function 133. At this step, the generating function 133 is implemented by causing the correction DAS 130 to read the computer program corresponding to the generating function 133 from the memory, and executing the computer program, for example.

As described above, in the first embodiment, the correction X-ray detector 100 includes the detector elements 121 that detect X-rays. The acquiring function 131 in the correction DAS 130 acquires the output values that correspond to the respective detector elements 121, and the determining function 132 then determines the detector elements to be used in generating the correction data based on the output values.

With such a configuration, when the detector elements 121 include some defective detector element, correction data can be generated using the detector elements 121 other than the defective detector elements 121, in the manner described above. With this configuration, it becomes possible to use the detector elements originally manufactured for the use in the X-ray detector 12 for imaging but rendered not usable because a defective detector element is included, as those for the correction X-ray detector 100, for example. Hence, the correction X-ray detector 100 can be manufactured at a lower cost. Therefore, according to the embodiment, it is possible to reduce the implementation cost of the correction X-ray detector 100.

Modification of First Embodiment

Explained in the first embodiment is an example in which the determining function 132 determines the detector elements using an expected value related to the output values, but the embodiment is not limited thereto. For example, the determining function 132 may also determine the detector elements by using an upper bound related to the output values as well.

In such a case, for example, the determining function 132 detects the detector element 121 the output value of which is smaller than the expected value, or greater than the upper bound that is greater than the expected value, from those to which the channel is assigned, and determines the detector elements 121 other than the detected detector element 121 as the detector elements to be used in generating the correction data.

The upper bound herein is a threshold for detecting the detector element 121 the output value of which is so high that it will cause an error in the signal processing performed in the correction X-ray detector 100. The upper bound is set in advance, for example, during the installation of the correction X-ray detector 100 in an installation site such as a hospital, based on an actual measurement or a standard value.

With this configuration, when the detector element array 120 includes some detector element 121 the output value of which is to cause an error in the signal processing, the detector element 121 is also excluded from the detector elements to be used in generating the correction data.

With such a configuration, by using only the detector elements 121 the output values of which do not result in errors in the signal processing, it becomes possible to generate more accurate correction data.

Second Embodiment

Explained in the first embodiment is an example in which the correction X-ray detector has one channel, but the embodiment is not limited thereto. For example, the correction X-ray detector may have a plurality of channels. Therefore, in the explanation hereunder, an example in which the correction X-ray detector has a plurality of channels will be explained as a second embodiment. In the explanation hereunder, the points that are different from those in the first embodiment will be mainly explained, and the elements that are the same as those in the first embodiment will be given the same reference numerals, and detailed explanations thereof will be omitted.

Figure 6:
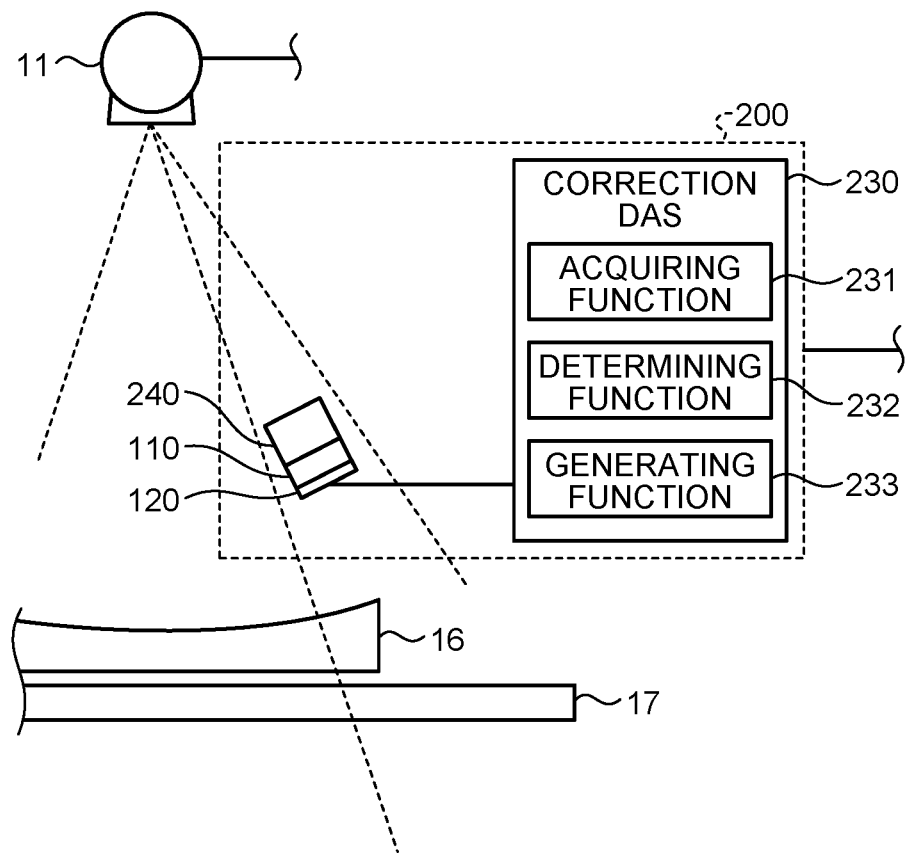
FIG. 6 is a schematic illustrating an exemplary configuration of a correction X-ray detector according to a second embodiment.

FIG. 6 is a schematic illustrating an exemplary configuration of a correction X-ray detector 200 according to the second embodiment.

For example, as illustrated in FIG. 6, the correction X-ray detector 200 is provided as a unit separate from the X-ray detector 12 for imaging, and is fixed to the rotating frame 13 included in the gantry 10, with a support member (not illustrated) such as a rigid frame. At this time, the correction X-ray detector 200 is provided so as not to enter the imaging range of the X-ray detector 12, between the X-ray tube 11 and the wedge 16. With this configuration, the X-rays being incident on the correction X-ray detector 200 do not experience the changes introduced by the wedge 16 or the X-ray aperture 17. It is also possible for the correction X-ray detector 200 to be integrated with the wedge 16 or the X-ray aperture 17.

The correction X-ray detector 200 detects the X-rays emitted from the X-ray tube 11, and generates, for each of the channels, the correction data for correcting the X-ray variations. The correction data generated by the correction X-ray detector 200 is then transferred, for each of the channels, to the console 40 via the DAS 18, and is used in correcting the variations of the dose and the energy spectrum of the X-rays to be emitted from the X-ray tube 11.

Specifically, the correction X-ray detector 200 includes the scintillator array 110, the detector element array 120, a collimator 240, and a correction DAS 230. The scintillator array 110 and the detector element array 120 both have the configurations explained in the first embodiment.

Figure 7:
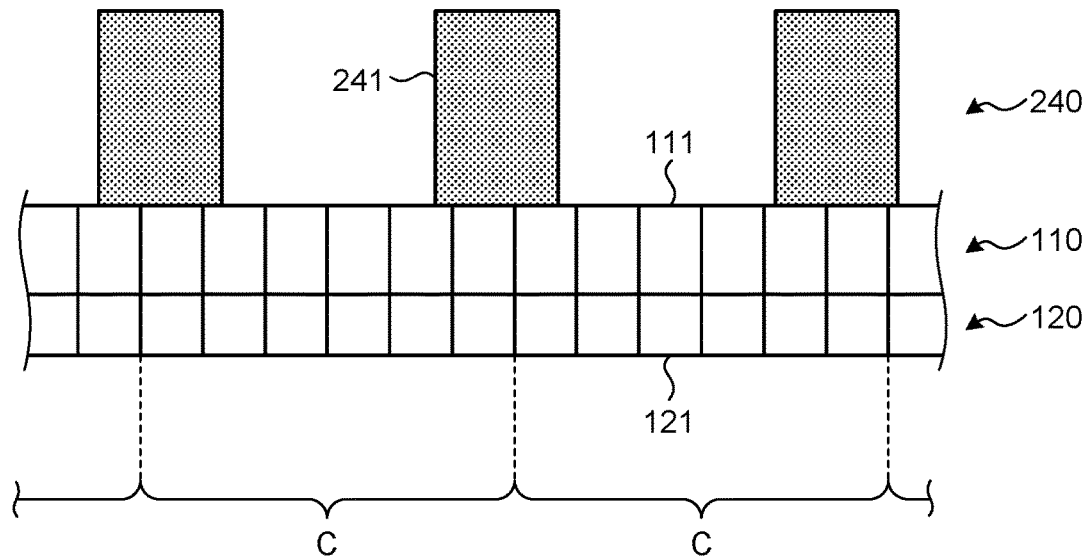
FIG. 7 is a schematic illustrating one example of a scintillator array, a detector element array, and a collimator included in the correction X-ray detector according to the second embodiment.

FIG. 7 is a schematic illustrating one example of the scintillator array 110, the detector element array 120, and the collimator 240 included in the correction X-ray detector 200 according to the second embodiment.

For example, as illustrated in FIG. 7, in this embodiment, the detector elements 121 included in the detector element array 120 are divided into a plurality of groups, and a separate one of the channels C is assigned to each of the groups.

In this embodiment, the correction X-ray detector 200 is further provided with the collimator 240 for preventing crosstalk between the channels.

The collimator 240 is disposed on the detector elements 121 of the detector element array 120 on the incoming side of the X-rays, and has a grid-like configuration that is partitioned into a plurality of sections by X-ray shields 241 that absorb the scattered X-rays.

Specifically, the collimator 240 is disposed on a surface of the scintillator array 110 on the incoming side of the X-rays. For example, the collimator 240 is a one-dimensional or a two-dimensional collimator. The collimator 240 is partitioned into sections in the same number as the number of the channels C, and is positioned so that the sections are positioned above the respective groups of the detector elements 121, which correspond to the channels, respectively.

In order to prevent the crosstalk between the channels reliably, it is necessary to position the sections of the collimator 240 precisely correspondingly to the groups of the detector elements 121, which are grouped correspondingly to the channels in advance. Furthermore, it is necessary to precisely position the X-ray shields 241 included in the collimator 240 in a manner inclined toward the focal point of the X-ray tube 11.

However, the detector elements used in an X-ray detector for imaging are usually smaller in size than those required in the correction X-ray detector, and the X-ray detector for imaging requires a larger number of detector elements. Therefore, it is difficult to position the collimator 240 precisely, and it is necessary to use a high-cost implementation technology.

To address this issue, in this embodiment, the correction X-ray detector 200 can be manufactured using a low-cost implementation technology lacking the capability of precisely positioning the collimator 240.

Referring back to FIG. 6, the correction DAS 230 is processing circuitry that generates the correction data based on the electric signals output from the respective detector elements 121 in the detector element array 120. Specifically, the correction DAS 230 generates correction data by amplifying the electric signals output from the respective detector elements 121 in the detector element array 120, and converting the amplified electric signals from the analogue signals into digital signals.

Specifically, the correction DAS 230 includes an acquiring function 231, a determining function 232, and a generating function 233. The acquiring function 231 is one example of the acquiring unit. The determining function 232 is one example of the determining unit. The generating function 233 is one example of the generating unit.

The acquiring function 231 acquires the output values that correspond to the respective detector elements 121 included in the detector element array 120.

Specifically, the acquiring function 231 acquires the output values of the electric signals output from the respective detector elements 121 included in the detector element array 120, the electric signals being output when the X-rays from the X-ray tube 11 become incident on the scintillator array 110 of the correction X-ray detector 200.

The determining function 232 determines the detector elements to be used in generating the correction data based on the output values acquired by the acquiring function 231.

Specifically, the determining function 232 performs thresholding to the output values acquired by the acquiring function 231, and determines the detector elements to be used in generating the correction data based on the result of the thresholding.

At this time, the determining function 232 determines, for each of the channels, the detector elements 121 to be used in generating the correction data, among those included in a group to which the channel is assigned.

Figure 8:
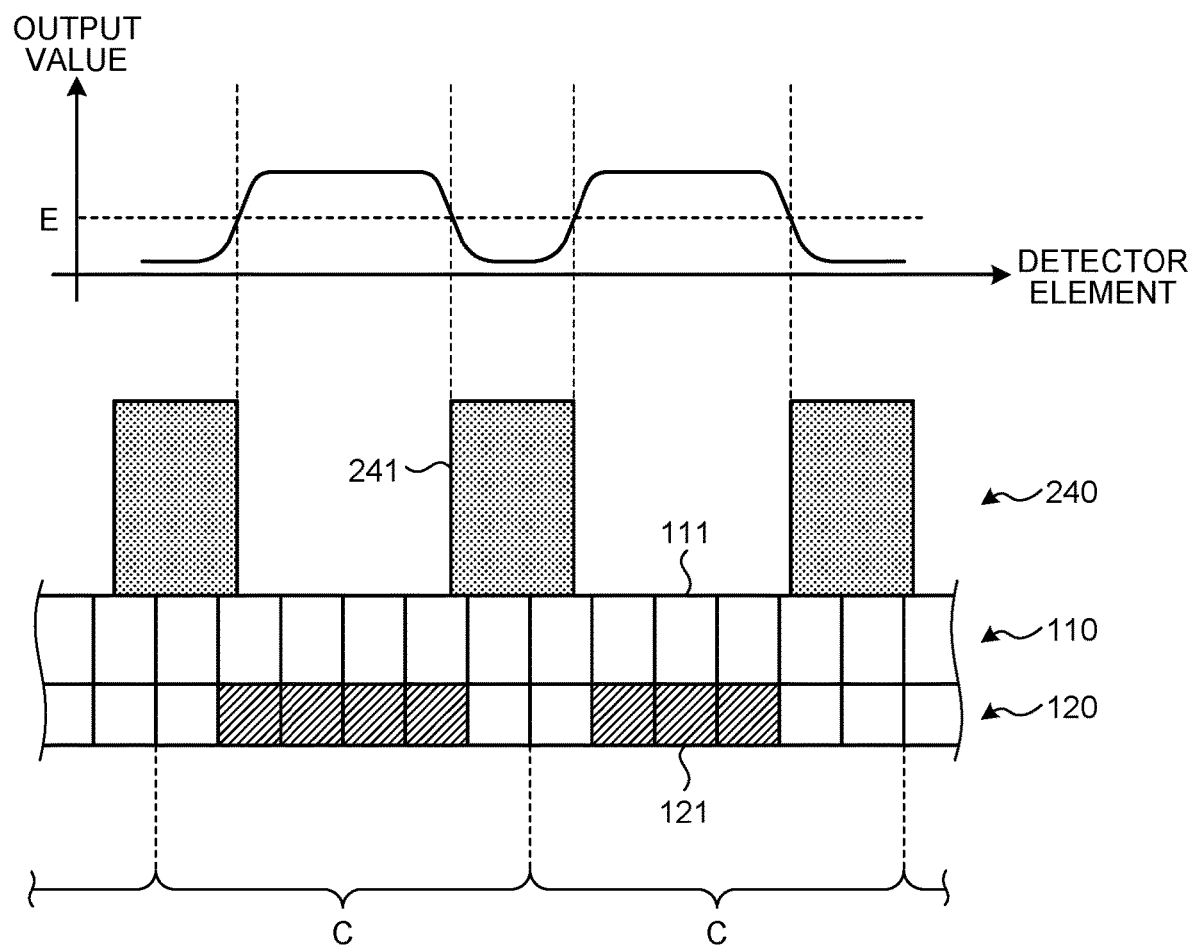
FIG. 8 is a schematic illustrating one example of how detector elements are determined by a determining function according to the second embodiment.

FIG. 8 is a schematic illustrating one example of how detector elements are determined by the determining function 232 according to the second embodiment.

For example, as illustrated in FIG. 8, the determining function 232 detects the detector elements 121 the output values of which are equal to or greater than the expected value E, among the detector elements 121 included in the group corresponding to each of the channels C. The determining function 232 then determines the detected detector elements 121 as the detector elements to be used in generating the correction data. In the example illustrated in FIG. 8, the detector elements 121 determined as the detector elements to be used in generating the correction data are hatched with diagonals.

The expected value E herein is a threshold for distinguishing whether a detector element 121 is sufficiently capable of detecting the X-rays, in the same manner as in the first embodiment. The expected value E is set in advance, for example, based on an actual measurement or a standard value during the installation of the correction X-ray detector 100 in an installation site such as a hospital.

With this configuration, the detector element 121 the output value of which is smaller than the expected value E are excluded from the detector elements used in generating the correction data, among those in the detector element array 120, because the detector element 121 is positioned where the X-rays are shielded by the X-ray shields 241 in the collimator 240. As a result, it becomes possible to generate the correction data using the detector elements 121 other than those at positions where the X-rays are shielded by the X-ray shields 241 in the collimator 240, among those included in the detector element array 120.

Furthermore, when the detector element array 120 includes some defective detector element 121 the output value of which is smaller than the expected value E, the detector element 121 is also excluded from the detector elements that are used in generating the correction data, in the same manner as in the first embodiment. As a result, in this embodiment, too, when the detector elements 121 include some defective detector element, correction data can be generated using the detector elements 121 other than the defective detector elements 121.

Referring back to FIG. 6, the generating function 233 generates, for each of the channels, the correction data based on the detector elements determined by the determining function 232.

Specifically, the generating function 233 generates, for each of the channels, correction data using the sum of the output values from the detector elements determined by the determining function 232. Alternatively, the generating function 233 may generate, for each of the channels, the correction data using the average or the maximum value of the output values from the detector elements, for example.

The correction data thus generated by the generating function 233 is then transferred, for each of the channels, to the console 40 via the DAS 18, and is stored in the memory 41. The correction data stored in the memory 41 is then read by the processing circuitry 44, and is used in correcting the variations in the dose and the energy spectrum of the X-rays to be emitted from the X-ray tube 11. To achieve this goal, in this embodiment, filters (not illustrated) having different X-ray shielding performance are mounted on the respective sections of the collimator 240, so that the X-rays exhibiting different energy spectra are detected by the respective channels, for example. It then becomes possible to detect changes in the tube voltage by comparing the pieces of correction data each having a different energy spectrum.

Figure 9:
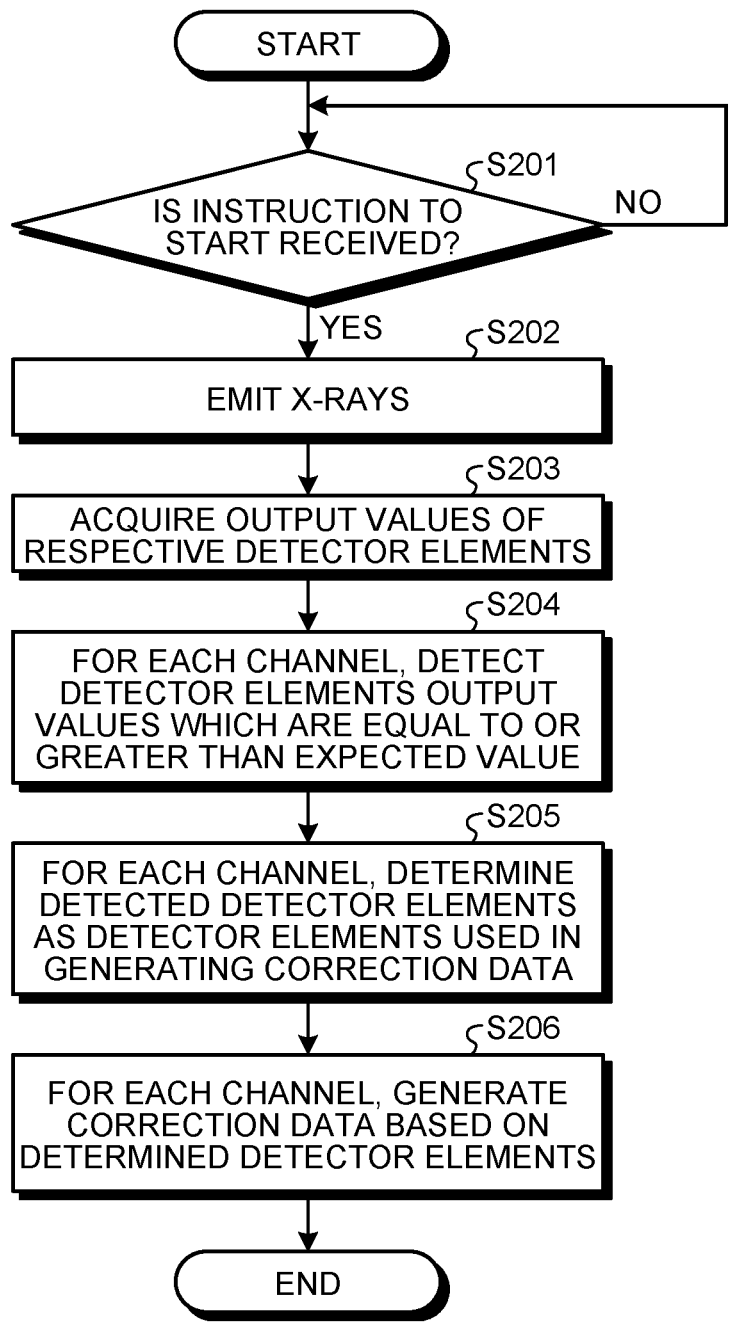
FIG. 9 is a flowchart illustrating the sequence of a process performed by an X-ray CT apparatus according to the second embodiment.

FIG. 9 is a flowchart illustrating the sequence of a process performed by the X-ray CT apparatus 1 according to the second embodiment.

The process explained below is performed, for example, during the installation of the X-ray CT apparatus 1 in an installation site such as a hospital, or during an adjustment of the X-ray CT apparatus 1.

For example, as illustrated in FIG. 9, to begin with, when an instruction to start is received from an operator via the input interface 43 (Yes at Step S201), the processing circuitry 44 causes the X-ray tube 11 to emit the X-rays toward the scintillator array 110 in the correction X-ray detector 200, by controlling the X-ray high voltage device 14 (Step S202). This step is a step corresponding to the control function 441. At this step, for example, the control function 441 is implemented by causing the processing circuitry 44 to read the computer program corresponding to the control function 441 from the memory 41, and executing the computer program.

The correction DAS 230 then acquires the output values that correspond to the respective detector elements 121 included in the detector element array 120 (Step S203). This step is a step corresponding to the acquiring function 231. At this step, for example, the acquiring function 231 is implemented by causing the correction DAS 230 to read the computer program corresponding to the acquiring function 231 from the memory, and executing the computer program.

The correction DAS 230 then detects, for each of the channels, the detector elements 121 the output values of which are equal to or greater than the expected value, from the detector elements 121 included in the group to which the channel is assigned, based on the acquired output values (Step S204). The correction DAS 230 then determines, for each of the channels, the detected detector elements 121 as the detector elements used in generating the correction data (Step S205). These steps are steps corresponding to the determining function 232. At these steps, for example, the determining function 232 is implemented by causing the correction DAS 230 to read the computer program corresponding to the determining function 232 from the memory, and executing the computer program.

The correction DAS 230 then generates, for each of the channels, the correction data based on the determined detector elements (Step S206). This step is a step corresponding to the generating function 233. At this step, for example, the generating function 233 is implemented by causing the correction DAS 230 to read the computer program corresponding to the generating function 233 from the memory, and executing the computer program.

As described above, in the second embodiment, the correction X-ray detector 200 includes the detector elements 121 that detect X-rays. The acquiring function 231 in the correction DAS 230 then acquires the output values that correspond to the respective detector elements 121, and the determining function 232 determines the detector elements to be used in generating the correction data, based on the output values.

With such a configuration, when the detector elements 121 include some defective detector element, correction data can be generated using the detector elements 121 other than the defective detector elements 121, in the same manner as in the first embodiment. With this configuration, for example, it becomes possible to use the detector elements originally manufactured for the use in the X-ray detector 12 for imaging but rendered not usable because a defective detector element is included, as those for the correction X-ray detector 200. Therefore, the correction X-ray detector 200 can be manufactured at a lower cost. Therefore, according to the embodiment, it is possible to reduce the implementation cost of the correction X-ray detector 200.

Furthermore, in the second embodiment, the detector elements 121 included in the detector element array 120 are divided into a plurality of groups, and a separate one of the channels C is assigned to each of the groups. The determining function 232 then determines, for each of the channels, the detector elements 121 to be used in generating the correction data, from those included in the group to which the channel is assigned.

With such a configuration, as described above, it becomes possible to generate the correction data using the detector elements 121 other than those positioned where the X-rays are shielded by the X-ray shields 241 in the collimator 240, among those included in the detector element array 120. With this configuration, the correction X-ray detector 200 can be manufactured using a low-cost implementation technology lacking the capability of precisely positioning the collimator 240. Therefore, according to the embodiment, the costs related to the implementation of the correction X-ray detector 200 can be further reduced.

First Modification of Second Embodiment

Explained in the second embodiment is an example in which the determining function 232 determines the detector elements using an expected value related to the output values, but the embodiment is not limited thereto. For example, the determining function 232 may also determine the detector elements by using an upper bound related to the output values as well.

In such a case, for example, the determining function 232 detects, for each of the channels, the detector elements 121 the output values of which are equal to or greater than the expected value and equal to or smaller than the upper bound that is greater than the expected value, from those included in the group to which the channel is assigned, and determines the detected detector elements 121 as the detector elements used in generating the correction data.

The upper bound herein is a threshold for detecting the detector element 121 the output value of which is so high that it will cause an error in the signal processing performed in the correction X-ray detector 200, in the same manner as in the modification of the first embodiment. The upper bound is set in advance, for example, during the installation of the correction X-ray detector 200 in an installation site such as a hospital, based on an actual measurement or a standard value.

With this configuration, when the detector element array 120 includes some detector element 121 the output value of which is to cause an error in the signal processing, the detector element 121 is also excluded from the detector elements to be used in generating the correction data.

With such a configuration, by using only the detector elements 121 the output values of which do not result in errors in the signal processing, it becomes possible to generate more accurate correction data.

Second Modification of Second Embodiment

Explained in the second embodiment is an example in which the acquiring function 231 acquires the output values of the electric signals output from the respective detector elements 121 included in the detector element array 120, the electric signals being output when the scintillator array 110 in the correction X-ray detector 200 is irradiated with the X-rays to be emitted from the X-ray tube 11, but the embodiment is not limited thereto.

For example, it is known that the position of the focal point of the X-ray tube 11 changes when the X-ray tube 11 is heated. When the position of the focal point changes, the incident angle of the X-rays incident on the scintillator array 110 in the correction X-ray detector 200 also changes. When the incident angle of the X-rays incident on the scintillator array 110 changes, the detector elements 121 having X-rays shielded by the X-ray shields 241 in the collimator 240 also change, among those included in the detector element array 120.

To address this issue, it is possible to generate the correction data considering the changes in the position of the focal point of the X-ray tube 11, for example.

In such a case, the acquiring function 231 changes the position of the focal point of the X-ray tube 11 to a plurality of different positions, and acquires the output values corresponding to the respective detector elements 121 included in the detector element array 120, at each of the different positions. The determining function 232 also determines the detector elements to be used in generating the correction data, for each of the different focal point positions. The generating function 233 also generates the correction data based on the detector elements determined by the determining function 232, for each of the different focal point positions.

The correction data thus generated by the generating function 233 is transferred, for each of the different focal point positions, to the console 40 via the DAS 18, and is stored in the memory 41. The correction data stored in the memory 41 is then read by the processing circuitry 44, and is used in correcting the variations in the dose and the energy spectrum of the X-rays to be emitted from the X-ray tube 11.

With such a configuration, by identifying the position of the focal point based on the temperature or the like of the X-ray tube 11 before performing imaging of the subject P, and using the correction data corresponding to the identified position, for example, it becomes possible to correct the variations in the dose and the energy spectrum of the X-rays to be emitted from the X-ray tube 11 more precisely.

Alternatively, for example, it is also possible to cause the determining function 232 to identify, after detecting the detector elements for each of the different focal point positions, the detector elements that are detected at all of such positions, and to determine the identified detector elements as the detector elements used in generating the correction data.

With such a configuration, even when the incident angle of the X-rays incident on the scintillator array 110 varies due to variations in the position of the focal point of the X-ray tube 11, the correction data is generated using only the detector elements 121 where the X-rays are not shielded by the X-ray shields 241 in the collimator 240. With this configuration, it becomes possible to correct the variations in the dose and the energy spectrum of the X-rays to be emitted from the X-ray tube 11 more precisely.

Third Embodiment

Explained in the first and the second embodiment is an example in which the correction X-ray detector includes the acquiring function, the determining function, and the generating function, but the embodiment is not limited thereto. For example, it is possible to provide the acquiring function, the determining function, and the generating function to the DAS 18 configured to generate the detection data based on the electric signal output from the X-ray detector 12 for imaging. Therefore, in the explanation hereunder, an example in which the DAS 18 includes the acquiring function, the determining function, and the generating function will be explained, as a third embodiment. In the explanation hereunder, the points that are different from those in the first and the second embodiments will be mainly explained, and the elements that are the same as those in the first and the second embodiments will be given the same reference numerals, and detailed explanations thereof will be omitted.

In this embodiment, an example in which the correction X-ray detector has one channel will be explained.

Figure 10:
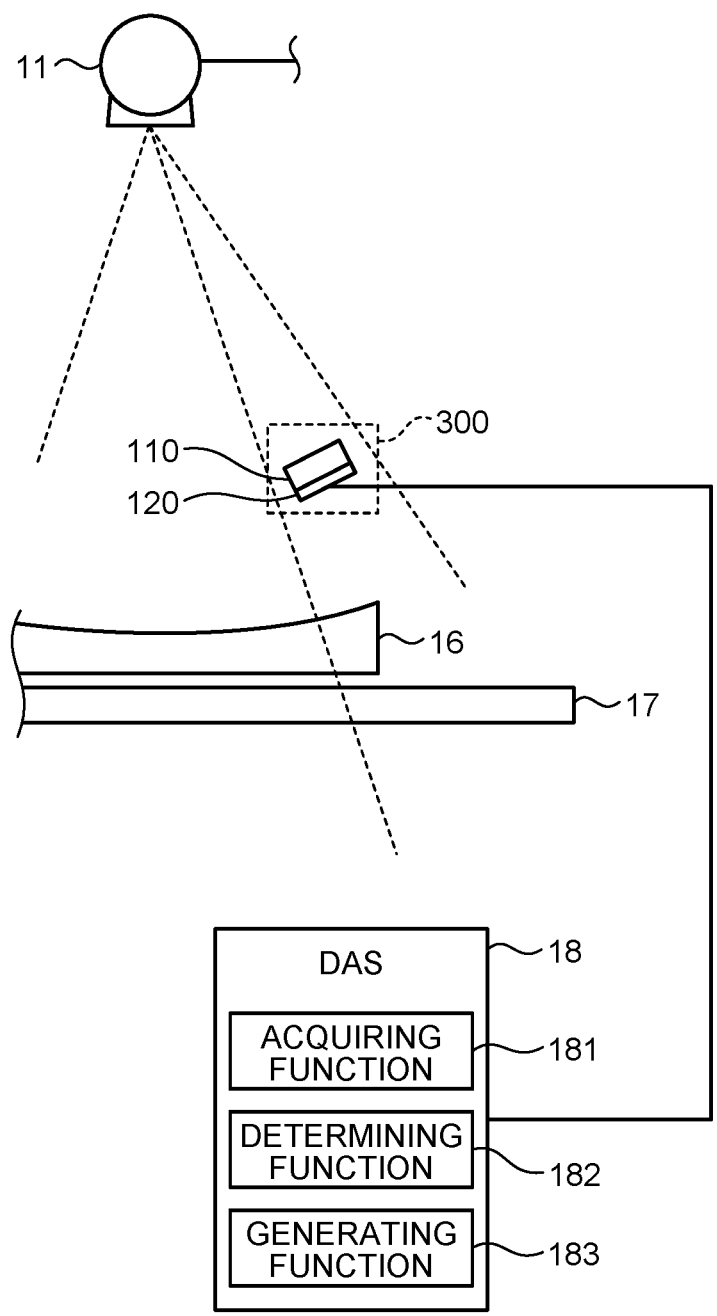
FIG. 10 is a schematic illustrating exemplary configurations of a correction X-ray detector and a DAS according to a third embodiment.

FIG. 10 is a schematic illustrating an exemplary configuration of a correction X-ray detector 300 and the DAS 18 according to the third embodiment.

For example, as illustrated in FIG. 10, in this embodiment, the correction X-ray detector 300 includes the scintillator array 110 and the detector element array 120. The scintillator array 110 and the detector element array 120 have the configurations explained in the first embodiment.

The DAS 18 includes an acquiring function 181, a determining function 182, and a generating function 183. The acquiring function 181 is one example of the acquiring unit. The determining function 182 is one example of the determining unit. The generating function 183 is one example of the generating unit.

The acquiring function 181, the determining function 182, and the generating function 183 have the same functions as the acquiring function 131, the determining function 132, and the generating function 133 explained in the first embodiment, except that these functions are implemented by the DAS 18.

The correction data thus generated by the generating function 183 is transferred to the console 40, and stored in the memory 41. The correction data stored in the memory 41 is then read by the processing circuitry 44, and used in correcting the variations in the dose of the X-rays to be emitted from the X-ray tube 11.

At this time, the DAS 18 is implemented by a processor, for example. With such an implementation, each of the processing functions included in the DAS 18 is stored in a memory (not illustrated) as a computer-executable program. The DAS 18 then implements the processing function corresponding to the respective computer programs by reading the computer programs from the memory, and executing the computer programs. In other words, the DAS 18 having read the computer programs comes to have the processing functions illustrated inside of the DAS 18 in FIG. 10.

As described above, in the third embodiment, the correction X-ray detector 300 includes the detector elements 121 that detect X-rays. The acquiring function 181 in the DAS 18 then acquires the output values that correspond to the respective detector elements 121, and the determining function 182 determines the detector elements to be used in generating the correction data based on the output values.

With such a configuration, when the detector elements 121 include some defective detector element, correction data can be generated using the detector elements 121 other than the defective detector elements 121, in the same manner as in the first embodiment. With this configuration, for example, it becomes possible to use the detector elements originally manufactured for the use in the X-ray detector 12 for imaging but rendered not usable because a defective detector element is included, as those for the correction X-ray detector 300. Therefore, the correction X-ray detector 300 can be manufactured at a lower cost. Therefore, according to the embodiment, it is possible to reduce the implementation cost of the correction X-ray detector 300.

Modification of Third Embodiment

Explained in the third embodiment is an example in which the correction X-ray detector has one channel, but the embodiment is not limited thereto. For example, the correction X-ray detector may have a plurality of channels.

In such a case, for example, the correction X-ray detector 300 includes the scintillator array 110, the detector element array 120, and the collimator 240. The scintillator array 110, the detector element array 120, and the collimator 240 have the configurations explained in the second embodiment.

Furthermore, the acquiring function 181, the determining function 182, and the generating function 183 have the same functions as the acquiring function 231, the determining function 232 and the generating function 233 explained in the second embodiment, except that these functions are implemented by the DAS 18.

The correction data thus generated by the generating function 233 is then transferred, for each of the channels, to the console 40, and stored in the memory 41. The correction data stored in the memory 41 is then read by the processing circuitry 44, and is used in correcting the variations in the dose and the energy spectrum of the X-rays to be emitted from the X-ray tube 11.

With such a configuration, it becomes possible to generate the correction data using the detector elements 121 other than those positioned where the X-rays are shielded by the X-ray shields 241 in the collimator 240, among those included in the detector element array 120, in the same manner as in the second embodiment. With this configuration, the correction X-ray detector 200 can be manufactured using a low-cost implementation technology lacking the capability of precisely positioning the collimator 240. Therefore, according to the embodiment, the costs related to the implementation of the correction X-ray detector 200 can be further reduced.

Fourth Embodiment

Explained in the third embodiment is an example in which the DAS 18 includes the acquiring function, the determining function, and the generating function, but the embodiment is not limited thereto. For example, it is possible to configure the processing circuitry 44 in the console 40 to further include the acquiring function, the determining function, and the generating function. Therefore, in the explanation hereunder, an example which the processing circuitry 44 in the console 40 includes the acquiring function, the determining function, and the generating function will be explained as a fourth embodiment. In the explanation hereunder, the points that are different from those in the first to the third embodiments will be mainly explained, and the elements that are the same as those in the first to the third embodiments will be given the same reference numerals, and detailed explanations thereof will be omitted.

In this embodiment, an example in which the correction X-ray detector has one channel will be explained.

Figure 11:
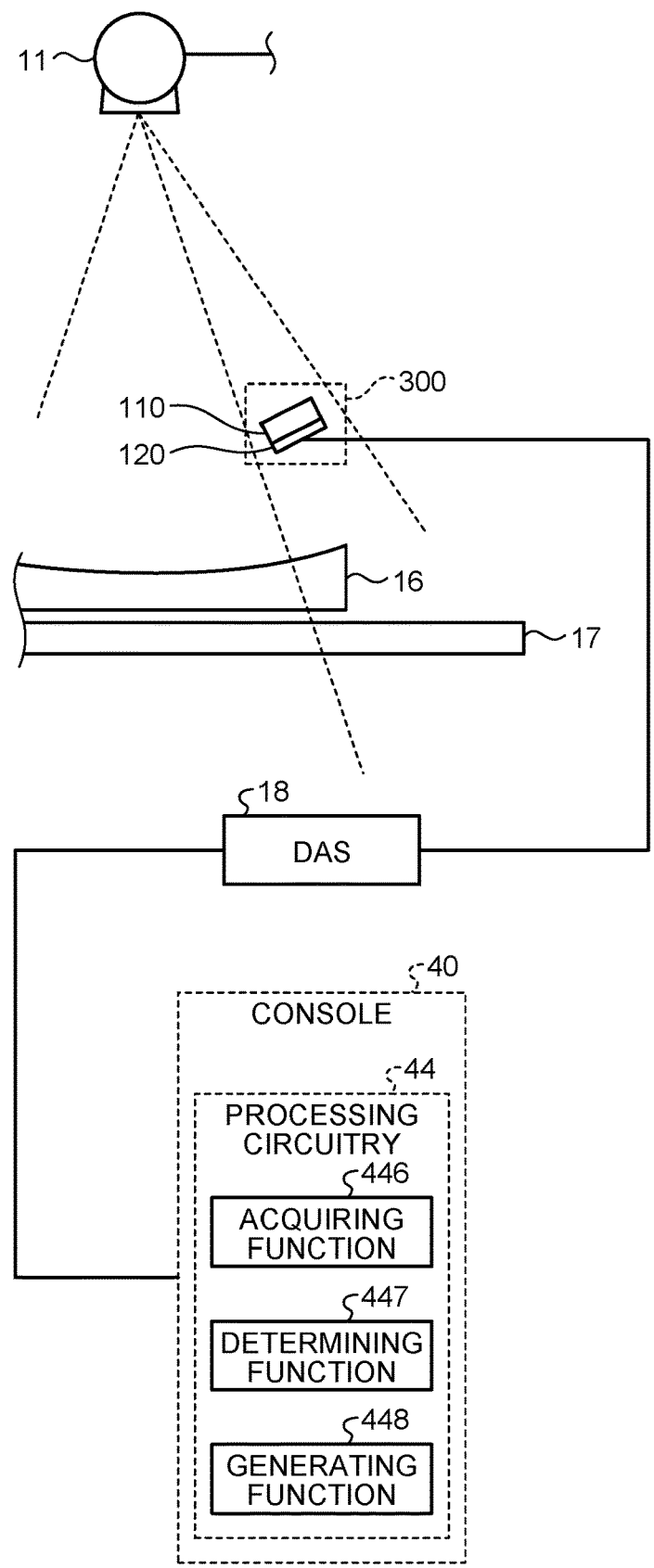
FIG. 11 is a schematic illustrating exemplary configurations of a correction X-ray detector and processing circuitry of a console according to a fourth embodiment.

FIG. 11 is a schematic illustrating exemplary configurations of the correction X-ray detector 300 and the processing circuitry 44 of the console 40 according to the fourth embodiment.

For example, as illustrated in FIG. 11, in this embodiment, the correction X-ray detector 300 includes the scintillator array 110 and the detector element array 120. The scintillator array 110 and the detector element array 120 have the configurations explained in the first embodiment.

The processing circuitry 44 in the console 40 includes an acquiring function 446, a determining function 447, and a generating function 448, in addition to the control function 441, the pre-processing function 442, the reconstructing function 443, the image processing function 444, and the display control function 445 illustrated in FIG. 1 (not illustrated in FIG. 11). The acquiring function 446 is one example of the acquiring unit. The determining function 447 is one example of the determining unit. The generating function 448 is one example of the generating unit.

The acquiring function 446, the determining function 447, and the generating function 448 have the same functions as the acquiring function 131, the determining function 132, and the generating function 133 explained in the first embodiment, except that these functions are implemented by the processing circuitry 44 in the console 40.

The correction data thus generated by the generating function 448 is stored in the memory 41. The correction data stored in the memory 41 is then read by the processing circuitry 44, and used in correcting the variations in the dose of the X-rays to be emitted from the X-ray tube 11.

The processing circuitry 44 is implemented by a processor, for example. With such an implementation, each of the processing functions included in the processing circuitry 44 is stored in the memory 41 as a computer-executable program. The processing circuitry 44 then implements the processing function corresponding to the respective computer programs by reading the computer programs from the memory 41, and executing the computer programs. In other words, the processing circuitry 44 having read the computer programs comes to have the processing functions illustrated inside of the processing circuitry 44 in FIG. 11.

As described above, in the fourth embodiment, the correction X-ray detector 300 includes the detector elements 121 that detect X-rays. The acquiring function 446 of the processing circuitry 44 in the console 40 then acquires the output values that correspond to the respective detector elements 121, and the determining function 447 determines the detector elements to be used in generating the correction data based on the output values.

With such a configuration, when the detector elements 121 include some defective detector element, correction data can be generated using the detector elements 121 other than the defective detector elements 121, in the same manner as in the first embodiment. With this configuration, for example, it becomes possible to use the detector elements originally manufactured for the use in the X-ray detector 12 for imaging but rendered not usable because a defective detector element is included, as those for the correction X-ray detector 300, so that the correction X-ray detector 300 can be manufactured at a lower cost. Therefore, according to the embodiment, it is possible to reduce the implementation cost of the correction X-ray detector 300.

Modification of Fourth Embodiment

Explained in the fourth embodiment is an example in which the correction X-ray detector has one channel, but the embodiment is not limited thereto. For example, the correction X-ray detector may have a plurality of channels.

In such a case, for example, the correction X-ray detector 300 includes the scintillator array 110, the detector element array 120, and the collimator 240. The scintillator array 110, the detector element array 120, and the collimator 240 have the configurations explained in the second embodiment.

The acquiring function 446, the determining function 447, and the generating function 448 have the same functions as the acquiring function 231, the determining function 232 and the generating function 233 explained in the second embodiment except that these functions are implemented by the processing circuitry 44 in the console 40.

The correction data thus generated by the generating function 448 is stored, for each of the channels, in the memory 41. The correction data stored in the memory 41 is then read by the processing circuitry 44, and is used in correcting the variations in the dose and the energy spectrum of the X-rays to be emitted from the X-ray tube 11.

With such a configuration, it becomes possible to generate the correction data using the detector elements 121 other than those positioned where the X-rays are shielded by the X-ray shields 241 in the collimator 240, among those included in the detector element array 120, in the same manner as in the second embodiment. With this configuration, the correction X-ray detector 200 can be manufactured using a low-cost implementation technology lacking the capability of precisely positioning the collimator 240. Therefore, according to the embodiment, the costs related to the implementation of the correction X-ray detector 200 can be further reduced.

Fifth Embodiment

Furthermore, according to the embodiments and the modifications described above, it is possible to change the purpose of the detector elements originally manufactured for the use in the X-ray detector 12 for imaging but rendered not usable because a defective detector element is included, to that for the use in the correction X-ray detector 100.

Explained below as a fifth embodiment is a detector element determining method for determining, when the purpose of use of the detector elements is to be changed in the manner described above, the detector elements used in generating the correction data in the correction X-ray detector 100.

FIG. 12 is a flowchart illustrating the detector element determining method according to the fifth embodiment.

For example, as illustrated in FIG. 12, the detector element determining method according to the embodiment includes Step S501 to Step S503.

At Step S501, a detector element array including a defective detector element is detected from a plurality of detector element arrays originally manufactured for the use in the X-ray detector 12 for imaging.

Specifically, at Step S501, the presence of a defective detector element is determined by using a given inspection method, and inspecting every detector element included in each of the detector element arrays originally manufactured for the use in the X-ray detector 12 for imaging. The detector element array determined not to include any defective detector element is determined to be used in the X-ray detector 12 for imaging. The detector element array determined to include a defective detector element is determined to be used in the correction X-ray detector 100.

At Step S502, the detector element array detected at Step S501 is implemented as a detector element array for the correction X-ray detector.

Specifically, at Step S502, the detector element array detected at Step S501 is implemented in the X-ray CT apparatus 1, by using the detected detector element array as a detector element array in the correction X-ray detector according to any one of the embodiments and the modifications described above.

At Step S503, the detector elements to be used in generating the correction data are then determined, from those included in the detector element array implemented at Step S502.

Specifically, at Step S503, the determining function is caused to determine the detector elements to be used in generating the correction data, in the manner explained in the embodiments or in the modifications.

For example, the detector element determining method according to the embodiment includes a step of causing the acquiring function to acquire a plurality of output values that correspond to the respective detector elements implemented at Step S502. At Step S503, the determining function is then caused to determine the detector elements to be used in generating the correction data based on the output values. For example, the determining function is caused to perform thresholding of the output values, and to determine the detector elements to be used in generating the correction data based on the result of the thresholding.

Furthermore, for example, the detector element determining method according to the embodiment also includes a step of causing the correction DAS to assign a channel to at least one part of the detector elements implemented at Step S502 to. In such a case, at Step S503, the determining function is caused to determine the detector elements to be used in generating the correction data from those to which the channel is assigned, in the manner explained in the first embodiment, the modification of the first embodiment, the third embodiment, and the fourth embodiment.

Alternatively, for example, the detector element determining method according to the embodiment may also include a step of dividing the detector elements implemented at Step S502 into a plurality of groups, and assigning a separate channel to each of the groups. In such a case, at Step S503, the determining function is caused to determine, for each of the channels, the detector elements to be used in generating the correction data, from those included in the group to which the channel is assigned, in the manner explained in the second embodiment, the modification of the second embodiment, the modification of the third embodiment, and the modification of the fourth embodiment.

Furthermore, for example, the detector element determining method according to the embodiment may also cause the acquiring function to change the position of the focal point of the X-ray tube to a plurality of different positions, and to acquire, for each of the different positions, the output values corresponding to the respective detector elements included in the detector element array implemented at Step S502, in the manner explained in the second modification of the second embodiment. In such a case, at Step S503, the determining function is caused to determine, for each of the different focal point positions, the detector elements to be used in generating the correction data, in the manner explained in the second modification of the second embodiment.

Other Embodiments

Explained in the embodiments is an example in which the correction X-ray detector is provided between the X-ray tube 11 and the wedge 16, but the embodiment is not limited thereto. For example, the correction X-ray detector may be disposed on the same surface as that on which the X-ray detector 12 for imaging is disposed. In such a configuration, the correction X-ray detector may be either provided as a separate unit, or be integrated with the X-ray detector 12.

Explained in the embodiments is an example in which each of the acquiring unit, the determining unit, and the generating unit disclosed herein are implemented as the acquiring function, the determining function, and the generating function of the processing circuitry (the correction DAS 130, the correction DAS 230, the DAS 18, the processing circuitry 44), but the embodiment is not limited thereto. For example, possible implementations of the acquiring unit, the determining unit, and the generating unit disclosed herein not only include the acquiring function, the determining function, and the generating function described in the embodiments, but also include implementations using hardware only, software only, or a combination of hardware and software.

Although, in the embodiments described above, the processing functions are explained to be implemented by a piece of processing circuitry, the processing functions may be implemented by using a combination of a plurality of independent processors as a piece of processing circuitry, and causing each of the processors to execute a computer program. Furthermore, each of the processing functions in the processing circuitry may be implemented in a manner distributed to or integrated into one or more pieces of processing circuitry. Furthermore, each of the processing functions in the processing circuitry may be implemented by a combination of hardware, such as a circuit, and software, for example. Furthermore, explained herein is an example in which a memory 41 stores therein a computer program corresponding to each of the processing functions, but the embodiment is not limited thereto. For example, a possible configuration includes a configuration in which a plurality of memory circuits are deployed in a distributed manner, and the processing circuitry reads a computer program from each of the memory circuits corresponding thereto and executes the computer program.

The term "processor" used in the explanation above means circuitry such as central processing unit (CPU), a graphics processing unit (GPU), an application specific integrated circuit (ASIC), a programmable logic device (such as a simple programmable logic device (SPLD) and a complex programmable logic device (CPLD)), and a field programmable gate array (FPGA). When the processor is a CPU, for example, the processor implements a function by reading a computer program stored in a memory circuit, and executing the computer program. When the processor is an ASIC, for example, the function is incorporated directly into the circuitry of the processor as a logic circuit, instead of storing the computer program in a memory circuit. The configuration of the processors in the embodiment is not limited to a configuration in which each of the processors is provided as a single piece of circuitry, but may also be a configuration in which a plurality of pieces of independent circuitry are combined as one processor, and are caused to implement the corresponding function. Furthermore, a plurality of elements illustrated in FIG. 1 may be integrated into one processor, and the processor may be caused to implement the functions of the elements.

Furthermore, in the embodiments and the modifications described above, the elements included in the illustrated devices are merely functional and conceptual representations, and do not necessarily need to be configured physically in the manner illustrated. In other words, specific configurations in which the devices are distributed or integrated are not limited to those illustrated, and the whole or a part thereof may be functionally or physically distributed or integrated into any units, depending on various loads or usage conditions. Furthermore, the whole or a part of the processing functions executed by these devices may be implemented by a CPU and a computer program executed by the CPU, or as hardware using a wired logic.

Furthermore, the whole or a part of the processes explained to be executed automatically in the embodiments and the modifications may also be performed manually, and the whole or a part of those explained to be executed manually may be executed automatically. Any other processes, control processes, specific names, and information including various types of data and parameters explained herein or illustrated in the drawings may be changed in anyway, unless explicitly described otherwise.

According to at least one of the embodiments described above, it is possible to reduce the implementation cost of a correction X-ray detector.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography (CT) apparatus, comprising:
   a main detector for imaging;
   a correction X-ray detector including a plurality of detector elements configured to detect X-rays, wherein the plurality of detector elements were originally manufactured for use in the main detector but were rendered not usable for the main detector because a defective detector element is included therein; and
   processing circuitry configured to
      acquire a plurality of output values respectively corresponding to the plurality of detector elements; and
      determine detector elements to be used in generating correction data based on the plurality of output values.

2. The X-ray CT apparatus according to claim 1, wherein the processing circuitry is further configured to generate the correction data based on the determined detector elements.

3. The X-ray CT apparatus according to claim 2, wherein the processing circuitry is further configured to generate the correction data using a sum, an average, or a maximum value of output values of the determined detector elements.

4. The X-ray CT apparatus according to claim 1, wherein the processing circuitry is further configured to:
   perform thresholding on the plurality of output values; and
   determine the detector elements to be used in generating the correction data based on a result of the thresholding.

5. The X-ray CT apparatus according to claim 1, wherein a channel is assigned to at least one part of the plurality of detector elements, and
   the processing circuitry is further configured to determine the detector elements to be used in generating the correction data, from the at least one part of the plurality of detector elements to which the channel is assigned.

6. The X-ray CT apparatus according to claim 1, wherein the plurality of detector elements are divided into a plurality of groups, and a plurality of channels are assigned to the plurality of groups, respectively, and
   the processing circuitry is further configured to determine, for each of the plurality of channels, the detector elements to be used in generating the correction data, from detector elements included in the respective groups.

7. The X-ray CT apparatus according to claim 6, further comprising a grid-shaped collimator disposed on an X-ray incident side of the plurality of detector elements, and divided into a plurality of sections by X-ray shields that absorb X-rays.

8. The X-ray CT apparatus according to claim 1, wherein the processing circuitry is further configured to:
   change a position of a focal point of an X-ray tube to a plurality of different positions;
   acquire, for each of the plurality of different positions, the plurality of output values respectively corresponding to the plurality of detector elements; and
   determine, for each of the plurality of different positions, the detector elements to be used in generating the correction data.

9. A detector element determining method for an X-ray computed tomography apparatus including a main detector for imaging, and a correction X-ray detector including a plurality of detector elements configured to detect X-rays, wherein the plurality of detector elements were originally manufactured for use in the main detector but were rendered not usable for the main detector because a defective detector element is included therein, the method comprising:
   detecting a detector element array including a plurality of detector elements including a defective detector element, from a plurality of detector element arrays manufactured to be used in the main detector;
   implementing the detected detector element array as the plurality of detector elements of the correction X-ray detector; and
   determining detector elements to be used in generating correction data, from the plurality of detector elements included in the implemented detector element array.

10. The detector element determining method according to claim 9, further comprising acquiring a plurality of output values respectively corresponding to the plurality of detector elements, wherein
   the determining further includes determining the detector elements to be used in generating the correction data based on the plurality of output values.

11. The detector element determining method according to claim 10, wherein the determining further includes:
   performing thresholding to the plurality of output values; and
   determining the detector elements to be used in generating the correction data based on a result of the thresholding.

12. The detector element determining method according to claim 9, further comprising assigning a channel to at least one part of the plurality of detector elements, wherein
   the determining further includes determining the detector elements to be used in generating the correction data, from the at least one part of the plurality of detector elements to which the channel is assigned.

13. The detector element determining method according to claim 9, further comprising dividing the detector elements into a plurality of groups, and assigning a plurality of channels to the plurality of groups, respectively, wherein
   the determining further includes determining, for each of the plurality of channels, the detector elements to be used in generating the correction data, from detector elements included in the respective groups.

14. The detector element determining method according to claim 10, wherein
the acquiring includes changing a position of a focal point of an X-ray tube to a plurality of different positions, and acquiring, for each of the plurality of different positions, the plurality of output values respectively corresponding to the plurality of detector elements, and
the determining further includes determining, for each of the plurality of different positions, the detector elements to be used in generating the correction data.

15. A correction X-ray detector, comprising:
a plurality of detector elements configured to detect an X-ray; and
processing circuitry configured to
change a position of a focal point of an X-ray tube to a plurality of different positions;
acquire, for each of the plurality of different positions, a plurality of output values respectively corresponding to the plurality of detector elements; and
determine, for each of the plurality of different positions, detector elements to be used in generating correction data based on the plurality of output values.

16. A detector element determining method, comprising:
detecting a detector element array including a plurality of detector elements including a defective detector element, from a plurality of detector element arrays manufactured to be used in an X-ray detector for imaging;
implementing the detected detector element array as a detector element array of a correction X-ray detector;
changing a position of a focal point of an X-ray tube to a plurality of different positions, and acquiring, for each of the plurality of different positions, the plurality of output values respectively corresponding to the plurality of detector elements; and
determining, for each of the plurality of different positions, detector elements to be used in generating correction data, from the plurality of detector elements included in the implemented detector element array, based on the plurality of output values.

* * * * *